US012636511B2

(12) United States Patent
Muntermann

(10) Patent No.: US 12,636,511 B2
(45) Date of Patent: May 26, 2026

(54) DEVICE FOR NUCLEAR MAGNETIC RESONANCE THERAPY

(71) Applicant: MedTec Medizintechnik GmbH,
Wetzlar (DE)

(72) Inventor: Axel Muntermann, Wetzlar (DE)

(73) Assignee: MedTec Medizintechnik GmbH,
Wetzlar (DE)

( * ) Notice: Subject to any disclaimer, the term of this patent is extended or adjusted under 35 U.S.C. 154(b) by 1071 days.

(21) Appl. No.: 17/582,637

(22) Filed: Jan. 24, 2022

(65) Prior Publication Data

US 2022/0143417 A1     May 12, 2022

Related U.S. Application Data

(63) Continuation of application No. PCT/EP2020/070935, filed on Jul. 24, 2020.

(30) Foreign Application Priority Data

Jul. 24, 2019     (DE) ..................... 10 2019 119 960.3

(51) Int. Cl.
*A61N 2/00*          (2006.01)
*A61H 1/00*          (2006.01)
(Continued)

(52) U.S. Cl.
CPC ............. *A61N 2/002* (2013.01); *A61H 1/005* (2013.01); *A61H 1/0222* (2013.01); *A61N 2/02* (2013.01);
(Continued)

(58) Field of Classification Search
CPC .......... A61N 2/002; A61N 2/02; A61N 2/004; A61N 2/006; A61H 1/005; A61H 1/0222; A61H 2001/0233; A61H 2201/0107; A61H 2201/10; A61H 2201/5061; A61H 2203/0456; A61H 2205/081; A61H 2201/0142; A61H 2201/1215;
(Continued)

(56) References Cited

U.S. PATENT DOCUMENTS 2,273,088 A      2/1942   Byers
3,060,926 A      10/1962  May
(Continued)

FOREIGN PATENT DOCUMENTS

CN      202776345 U     3/2013
CN      105288854 A     2/2016
(Continued)

OTHER PUBLICATIONS

Communication pursuant to R 71(3) EPC dated Mar. 20, 2023 for European Patent Application No. 20 746 186.4 (7 pages).
(Continued)

*Primary Examiner* — Carrie R Dorna
*Assistant Examiner* — Joshua Daryl D Lannu
(74) *Attorney, Agent, or Firm* — TAYLOR & EDELSTEIN, PC

(57)                ABSTRACT

A device for nuclear magnetic resonance therapy includes: a device configured to create an alternating magnetic field; a device configured to create a magnetic field as a sweep field running transversely to the alternating magnetic field; and a device configured to stretch a user.

12 Claims, 9 Drawing Sheets

(51) Int. Cl.
  *A61H 1/02* (2006.01)
  *A61N 2/02* (2006.01)

(52) U.S. Cl.
  CPC ............... *A61H 2001/0233* (2013.01); *A61H 2201/0107* (2013.01); *A61H 2201/10* (2013.01); *A61H 2201/5061* (2013.01); *A61H 2203/0456* (2013.01); *A61H 2205/081* (2013.01)

(58) Field of Classification Search
  CPC ........ A61H 2201/123; A61H 2201/149; A61H 2201/1619; A61H 2201/1621; A61H 2201/1642; A61H 2201/5007; A61H 2203/0468; A61H 2230/00; A61H 1/0292
  See application file for complete search history.

(56) References Cited

U.S. PATENT DOCUMENTS

| | | | |
|---|---|---|---|
| 3,404,679 | A | 10/1968 | Bevilacqua |
| 4,144,880 | A | 3/1979 | Daniels |
| 9,724,534 | B2 * | 8/2017 | Jacobson ................. A61N 2/02 |
| 10,376,709 | B2 | 8/2019 | Muntermann |
| 2003/0195410 | A1 * | 10/2003 | Winter .................... A61N 2/00 600/410 |
| 2004/0199070 | A1 | 10/2004 | Krockel |
| 2005/0080333 | A1 | 4/2005 | Piron et al. |
| 2008/0176721 | A1 * | 7/2008 | Boren .................. A61H 1/0218 482/92 |
| 2013/0184615 | A1 | 7/2013 | Johnson |

FOREIGN PATENT DOCUMENTS

| | | |
|---|---|---|
| CN | 108144184 A | 6/2018 |
| CN | 104905902 B | 3/2019 |
| DE | 10 2005 016 337 A1 | 10/2006 |
| DE | 10 2009 060 544 A1 | 6/2011 |

OTHER PUBLICATIONS

Korean Office Action dated Sep. 27, 2022 for Korean Patent Application No. 2022104537 (8 pages).

English translation of Korean Office Action dated Sep. 27, 2022 for Korean Patent Application No. 2022104537 (4 pages).

International Search Report, including an English translation, dated Dec. 21, 2020 for International Application No. PCT/EP2020/070935 (10 pages).

Written Opinion of the International Searching Authority dated Dec. 21, 2020 for International Application No. PCT/EP2020/070935 (7 pages).

International Preliminary Report on Patentability dated Jul. 5, 2021 for International Application No. PCT/EP2020/070935 (13 pages).

* cited by examiner

DEVICE FOR NUCLEAR MAGNETIC RESONANCE THERAPY

CROSS REFERENCE TO RELATED APPLICATIONS

This application is a continuation of International Application No. PCT/EP2020/070935 filed on Jul. 24, 2020, which is incorporated in its entirety herein by reference. International Application No. PCT/EP2020/070935 claims the priority of German Patent Application No. DE 10 2019 119 960.3 filed on Jul. 24, 2019, which is incorporated in its entirety herein by reference.

BACKGROUND OF THE INVENTION

1. Field of the Invention

The invention relates to a device for nuclear magnetic resonance therapy and a process for the control of the device. The invention relates in particular to a device for the treatment of degenerative changes in the skeletal and musculoskeletal system, damage to ligaments, muscles, sinews and nerves, pathological changes in spinal discs and vertebrae, sports injuries and injuries caused by accidents, pathological changes in the bony structures, and for the treatment of patients with arthrosis.

2. Description of the Related Art

Devices for nuclear magnetic resonance therapy are known. In particular, the document DE 10 2009 060 544 B4 shows a device for the creation of nuclear magnetic resonance in the tissue due for treatment.

This is a device which creates a magnetic field with a uniform field strength in a treatment area. This magnetic field is overlaid by an alternating field irradiated at right angles to the magnetic field. A "sweeping" of the first field in the form of minor changes in the field strength, for example in the form of a saw tooth, produces a resonance condition at every cycle. It has also been shown that this so-called sweep frequency, via which a rapid adiabatic resonance is achieved, contributes to the success of the treatment.

Contrary to imaging magnetic resonance scanners, devices which create nuclear magnetic resonances for therapeutic or cosmetic purposes generally work with relatively low field strengths, in particular with field strengths which lie in the mT area.

In contrast to the processes for nuclear magnetic resonance therapy mentioned above, other processes are known in which a part of the body to be treated is placed inside an air-core coil whereby a pulsating direct current flows through the air-core coil. The magnetic field is therefore uniform inside the coil. In particular, alternating magnetic field is present. Thus in devices according to this principle, which is also known as the "PST process" (PST=pulsating signal therapy), this is a different field of activity and application in which nuclear magnetic resonance therapy is fundamental.

SUMMARY OF THE INVENTION

In some exemplary embodiments provided according to the invention, a device for nuclear magnetic resonance therapy includes: a device configured to create an alternating magnetic field; a device configured to create a magnetic field as a sweep field running transversely to the alternating magnetic field; and a device configured to stretch a user.

In some exemplary embodiments provided according to the invention, a module for stretching a user includes a frame configured to be placed on a casing and having at least two boards which form a table, whereby one of the boards is movable in relation to the other board by a drive.

In some exemplary embodiments provided according to the invention, a process for controlling a device for nuclear magnetic resonance therapy includes: creating an alternating magnetic field and a static sweep field transverse to the alternating field by which nuclear magnetic resonances are created in a tissue of a user; and stretching the user by a pulling device activated by a control device during the creation of the nuclear magnetic resonances.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1:
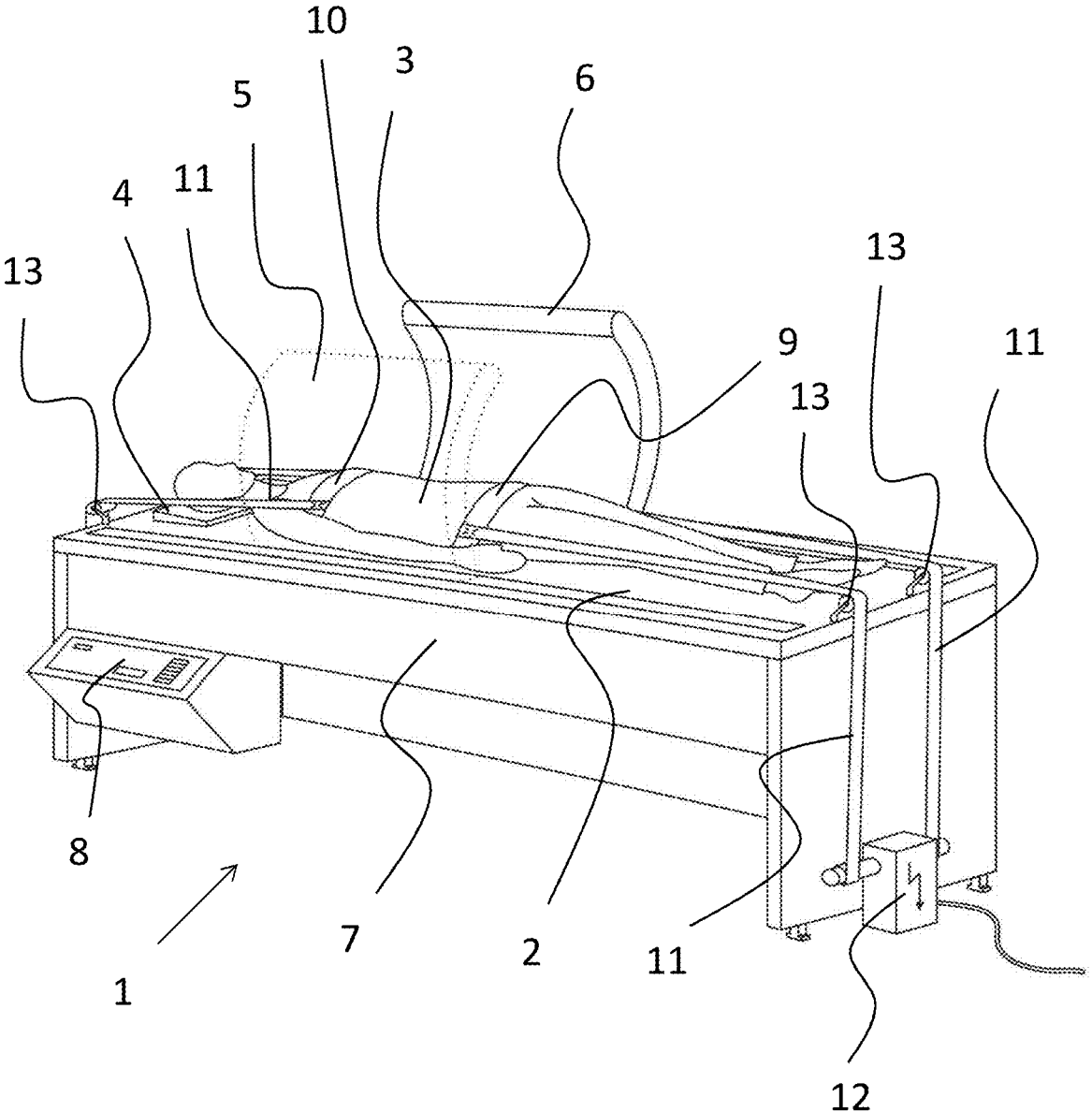
FIG. 1 illustrates a perspective view of an exemplary embodiment of a device for nuclear magnetic resonance therapy.

Exemplary embodiments provided according to the invention are based on a device for the further improvement of nuclear magnetic therapy.

Exemplary embodiments provided according to the invention enhance therapeutic outcomes, particularly in the case of degenerative changes in the skeletal and musculoskeletal system, damage to ligaments, muscles, sinews and nerves, pathological changes in the spinal discs and vertebrae, sports injuries and injuries caused by accidents, pathological changes in the bony structures as well as for the treatment of patients with arthrosis.

Exemplary embodiments disclosed herein provide a device for the purpose of nuclear magnetic resonance therapy, by a module, particularly for the creation of a cyclical or permanently metered stretching of a user, as well as by a process for the control of a device with the purpose of nuclear magnetic resonance therapy.

The invention relates to a device for nuclear magnetic resonance therapy. This comprises an entity for the creation of an alternating magnetic field as well as an entity for the creation of a field running transversely to the alternating magnetic field, in particular a sweep field.

The device for the creation of an alternating magnetic field comprises a coil. The coil can, for instance, be arranged below a table on which the user lies during the treatment.

In order to create a sweep field the apparatus can comprise two coils arranged in a Helmholtz configuration. The spools are activated in such a manner that the magnetic field created internally which is uniform has a basic value which is periodically raised and lowered. It is obvious that in the case of this configuration it is also possible to create the basic value wholly or partially by the incorporation of permanent magnets.

In particular the apparatus takes such a form that the sweep field is modulated in the form of a saw tooth profile in which the alternating field is switched on during the falling flanks of the sweep field.

The device provided according to the invention also comprises an apparatus which provides a static stretching or an impulsed stretching of a user which can be set in a metered or controlled manner. An apparatus for stretching a user is understood to be an entity by which a tractive force, in particular a pulsed or permanently constant force, is imposed in a longitudinal direction on parts of a patient's body.

The apparatus to stretch the user can comprise differently shaped straps and fastenings which can be applied, as well as at least one pulling device for at least one strap.

According to some embodiments provided according to the invention, at least one strap is equipped with an electrical or mechanical release system or rapid release system. The release procedure can be signaled by an acoustic signal or an optical message to the technical staff or the doctor treating the patient.

The strap is released when a maximum force determined by the design and/or an adjustable maximum force is reached. In this way an unintentional over-stretching of the user can be avoided.

A further safety release can be achieved by sensors applied to the skin of the back or via other measuring devices, for example by measuring the muscle contraction.

According to some embodiments, the pulling device is electrically powered and is therefore able to automatically apply, particularly, a pulsating and/or controlled permanent tractive force to the user, for example at an impulse frequency range of 0-1 kHz, in three directions or on three planes. The degree of the displacement can be displayed by an acoustic or optical feedback.

As primarily the lumbar vertebrae and the cervical vertebrae are reported to respond to treatment in the event of herniated discs, the individual reclining surfaces can be adjusted to meet these requirements. In some embodiments, which can have up to five or more than five individual reclining surfaces, a transversely arranged bearing point or bearing post is positioned in the middle of each board so that the individual boards of the reclining surface can be moved mechanically or electrically. In this way, a part of the spinal column, or particularly individually affected vertebrae, can be specifically reached in the best possible quality and intensity of the stretching for the affected vertebra.

The apparatus for stretching is particularly designed such that by the apparatus according to some embodiments the patient's spinal column can be moved and/or stretched in three planes. In order to achieve this, the apparatus comprises straps which can be fastened around the upper body and hips as well as the feet and head area of the user. Certain straps are equipped with an electrical or mechanical release or rapid release system whereby an unintentional over-stretching of the user can be avoided.

In some embodiments, the apparatus is configured to stretch the user's legs. To achieve this, the apparatus includes a strap which is placed around the hips as well as straps and loops which can be placed around the user's ankles.

The tensioning movement can also be executed mechanically or electrically in three planes or directions a spindle drive.

Thus vertebral displacements or muscular tension can be included in the therapy program.

Injuries to the vertebrae or muscles that occur frequently in sports injuries or accident injuries can also be treated this way.

Archived necessary therapeutic movement sequences during the treatment by the movement and supporting apparatus can be implemented safely, effectively and without problems in this way.

It is also possible to stretch the patient's entire body in which a strap retaining system is fastened in the area of the head, forehead and chin or a strap is secured round the upper body and two further straps round the ankles.

It is evident that the straps can have any form and that, in particular, solid components that can be placed around the body can also be used.

The knowledge is fundamental to the invention that particularly in the treatment of degenerative changes of the skeletal and locomotor system, damage to ligaments, muscles, sinews, tendons and nerves, pathological changes in the spinal discs and vertebrae, sports injuries and injuries caused by accidents, pathological changes in the bony structures as well as for the treatment of patients with arthrosis, there is a synergy effect concerning the creation of nuclear magnetic resonances in the region of the tissue to be treated, in particular in the regions of the bones, cartilage, muscles, tendons and nerves to be treated as well as in disorders of or damage to the spinal column, at the same time as contemporaneous mechanical stimulation by permanent or pulsating vibrations in the area of 0-1 kHz as stretching in the parts of the body that are affected and that this effect leads to a distinctly faster regeneration of affected tissue.

Thus vertebral displacements or muscular tension can be included in the therapy program.

Injuries to the vertebrae or muscles that occur frequently in sports injuries or accident injuries can also be treated in this way.

Archived necessary therapeutic movement sequences during the treatment by the movement and supporting apparatus can be implemented safely, effectively and without problems in this way.

More recent investigations and studies show that as a result of the nuclear magnetic resonance effect disrupted cycles of the circadian rhythm of cells are resynchronized, pathological conditions are beneficially influenced and the ATP as well as the oxygen level in the cells are increased, all of which provides major beneficial support to cell metabolism.

Mechanical pre-tensioning by traction or pulsating vibrations during and as a supplement to nuclear magnetic resonance treatment very significantly increases the piezoelectrical effects in joints and areas of the bones by tensioning and pressure (movement) and thus increases the metabolic process in the affected tissue.

In some embodiments, the apparatus for stretching the user includes one or at least one board which can be moved in a linear direction by a spindle which in some embodiments can be moved in three planes or three directions to stretch the user.

The apparatus for stretching the user comprises at least one board which can be moved in a linear direction and which can also be moved by one or more spindles vertically and/or horizontally or moved in in a linear direction in three planes or three directions as a movable head part, middle part, foot part or front part of the reclining area to stretch the user.

As it is said that particularly the lumbar vertebrae and the cervical vertebrae respond to treatment in the event of a herniated disc, the individual reclining areas can be adjusted to suit these requirements. In some embodiments, which can have up to five or more than five possible individual reclining surfaces, a transversely arranged bearing point or bearing post is positioned in the middle of each board so that the individual boards of the reclining surface can be moved mechanically or electrically round the axis of the support point. In this way a part of the spinal column, or particularly individually affected vertebrae, can be specifically reached in the best possible quality and intensity of the stretching for the affected vertebra.

A section of a reclining surface can be made available by the board. The board is, in particular, provided with holding or retaining points or other retaining facilities such as eyelets through which a strap can be threaded.

In some embodiments, it is provided that for the purpose of nuclear magnetic resonance therapy the device comprises at least two or more boards which in some embodiments can be moved vertically and/or horizontally or in three planes, of which at least one board can be moved by one or more spindles in a linear direction manually, mechanically or by electrically powered motors.

In some embodiments, the board/boards are positioned using the spindles by at least one activating device at the head or foot end or at one side of the reclining or traction module.

The tensile force of the traction is controlled by a pressure cell, a strain gage or tensile force measuring device. The tensioning or stretching length can be set in the range from 0 to 30 cm or more via an analogue or digital measuring scale.

According to some embodiments, the tensile force, the twist points, the length of the extension, the torsion and/or the impulse frequency can be controlled in particular using an electronic chip card reader. In particular, several servomotors or step motors can be activated and program cycles saved. In addition, information concerning the torsion, the length of the path or tension and the angle of traction, a tensile force of the traction from 0-60 kg, a pulsating traction movement between 0-1 kHz, time sequences, protective safety devices and an emergency stop switch, ergonomic changes in the reclining surface and/or the changes in height in the foot and the head part can be saved in the control device. Each of these can be allocated to patient data stored in the memory. Thus individual treatments can be easily guaranteed.

The values before and/or during the treatment can be set, amended and controlled via a control computer with a display.

In some embodiments, these values can be established automatically before the treatment by sensors on the patient who is about to be treated and the corresponding data saved automatically via the device's electronic system or the chip card relevant to the treatment.

The data about the settings for the above-mentioned values are saved for each patient in an electronic memory or on a chip card; this ensures that the settings can be reproduced before and during the treatment and the course of the treatment. Consequently the device can be switched off manually and electronically via sensors.

The user can, for instance, be secured on a board, in particular a central board, in particular with adjustable fixing devices, for example at the hips. On a different board the user can be secured either at the legs or shoulders or head.

In addition, the device provided according to the invention includes a retaining strap system designed to be applied to the forehead or head. This can be a collar which is applied to the chin and forehead and which secures the head and enables tension to be applied via the cervical vertebrae.

By way of a displacement of one board compared with other boards the user can be stretched either permanently or in pulses either with or without the nuclear magnetic resonance system.

The boards may be provided with padding, in particular with foamed plastic.

One or more protective joint components below or between the boards, e.g. in the form of rubber or plastic lips or bellows, can ensure that no dirt can fall through the gap between the boards and into the treatment device positioned underneath.

The location and position of the movable boards can be changed, in particular by one or more drives on the end.

In particular, provision is made for a drive with a threaded spindle by which the position of one board can be changed and/or moved either manually or by an electric motor, particularly permanently or in pulses, in a linear direction in different planes or directions.

In some embodiments, the drive, particularly a threaded spindle or a bar to move the movable board is arranged at least in sections under a different and non-movable board.

In some embodiments, it is provided that the drive is arranged on the front, that is to say in front or at the rear or on one of the longitudinal sides on the device for nuclear magnetic resonance therapy whereby a central or one or more end boards can be moved by a mechanism arranged under a fixed board.

In this way an operating device can be provided which is arranged at the front or the rear of the device for nuclear magnetic resonance therapy, that is to say at the side from which the user is stretched and also from which the strap is normally applied.

In some embodiments, the device for stretching the user takes the form of a module capable of being positioned on a casing.

According to some embodiments, the board of the foot part is connected to an air bag, plastic bag or bellows which can be filled with air or liquid by electrical or mechanical means to lift the foot part vertically by between 1 and 60 cm compared with the rest of the reclining surface.

A corresponding mechanical, electrical or electronic device can be provided for this purpose.

This function can also be achieved by, for example, a mechanical scissor lift, a telescopic arrangement or similar lifting system that can specifically raise the foot part.

This device relieves the load on the spinal column in the event of a disorder or injury of a spinal disc.

In this way no other supports such as cube-shaped pads or similar are needed during treatment, thus significantly increasing the patient's comfort while he/she is lying down.

According to some embodiments, the head part can be raised by an air bag, plastic bag or bellows which can be filled manually or by a mechanical or electric air or liquid pump. The head area can be supported in this way.

The volume of air for lifting the head or foot can be controlled and monitored by an electronic or mechanical manometer or other pressure measuring system.

According to some embodiments, a module is provided which comprises a frame to which at least one movable board is allocated.

In this way that device for stretching the patient can be supplied as a retrofitting set which replaces the pad of the device or which is placed under the pad of the device.

In particular the device for stretching the patient takes such a form that a periodically changing force can be created by a pulling device.

By way of a periodically changing force which, for example can be created by an electrical drive and corresponding control system, a vibration is concentrated on the regions of the body to be treated and the cartilage and tissue is stimulated by nuclear magnetic resonances during the treatment in such a manner that the division rate and therefore the formation of body cells is significantly improved in the most varied types of tissue to be treated.

The frequency of the periodically changing force is particularly between 0.01 and 1 kHz.

In some embodiments, the device for stretching the user comprises an actuator for creating a vibration applied to the pulling device.

Such embodiments provided according to the invention therefore relate to a device having a pulling device for creating a force and a further actuator for concentrating vibrations which are superimposed on the force created by the pulling device.

Mechanical eccentric discs with lifting rods are possible for creating the traction.

In such embodiments, the traction speed can be controlled electrically, mechanically or electronically.

Actuators are provided which include a weight that can be magnetically stimulated to vibrate. Moving coil actuators can, in particular, be used.

It is certainly also possible to create a periodically changing force using an electrically powered device. However, a change of force with a very high frequency can be created in a much simpler manner using an actuator without the danger that this is severely weakened by attenuation within the pulling device.

This applies in particular if the actuators are installed relatively close to the straps for the user or are integrated into the straps. The distance of the actuator from the strap may be less than 50 cm.

The actuator is particularly designed to vibrate with a frequency of between 0.1 and 1 kHz, for example between 1 and 200 Hz.

In some embodiments, the device comprises a control device for the entity to create the alternating magnetic field and for the sweep field which is also designed to control the device for stretching the user at the same time.

All treatment parameters can in this way be easily entered via a single control device and, if necessary, automatically entered e.g. by chip cards or storage devices.

It is also possible that there is a beneficial effect on the success of the treatment if the frequency with which the force used to stretch the user is modulated and synchronized to the frequency of the sweep field. By this it is also understood that the frequency with which the stretching force is modulated is a full multiple or a fraction of the frequency of modulation of the sweep field.

In some embodiments, the force for stretching the user is modulated in such a manner that this force increases or decreases always in the falling flanks of the sweep field.

In some embodiments, the device for the nuclear magnetic resonance therapy is designed as a table whereby two side parts are arranged at the side of the table, each of which include a coil. These coils positioned at the side are arranged in a Helmholtz configuration and create the sweep field. An alternating magnetic field is irradiated transversely into the sweep field by at least one coil under the table.

The invention also relates to a module for stretching a user which can be used in particular for a device for nuclear magnetic resonance therapy as described previously.

The module particularly takes the form of a retrofit set capable of being positioned on a casing of a device for treatment with nuclear magnetic resonances.

The module comprises a frame capable of being positioned on a casing with at least two boards, for example three boards, which form a reclining surface whereby one of the boards can be moved in relation to the other board or boards by a drive.

In some embodiments, the module comprises three or more than three and in particular five boards whereby at least one central or front board or each of the boards can be moved, in particular on rails which are arranged on the frame, in particular by a drive having a spindle or bar running at least in sections under a fixed board.

A strap can be attached to the movable board and to at least one of the other boards.

The user can then be stretched in measured amounts by the displacement of the one board compared with the other boards.

In some embodiments, the module comprises at least two boards whereby one, particularly a central board or several boards, can be moved.

According to some embodiments, one or more end boards can be moved.

In embodiments with a central movable board, it is possible for a part of the drive, in particular a device for measuring force, to be located under one of the non-movable boards. In this way a compact configuration is achieved.

The movable board or boards can be moved in particular on rails which are arranged on the frame.

A spindle drive is particularly used as the drive.

The length of the stretching and the force of the impulses and/or the tensile forces can be monitored and checked by suitable measurement and control devices; a status display in an acoustic and/or optical form is possible and provided in some embodiments.

The invention also relates to a process for the control of a device for nuclear magnetic therapy, in particular of a device described previously.

An alternating magnetic field and a static sweep field transverse to the alternating field are created by a control device. Nuclear magnetic resonances are created in the tissue of a user by these magnetic fields. At the same time the user is stretched by a pulling device activated by the control device during the creation of the nuclear magnetic resonances.

The control device is programmable in particular with regard to the duration of the treatment, the frequency of the modulation of the sweep field and, optionally, also the frequency of the modulation of the force exercised by the device to stretch the user.

In particular, provision is made for the automatic termination of the treatment. The pulling device may also be switched off automatically.

Provision is also made in particular for the coordination of the frequency of the modulation of the force used to stretch the user with the frequency of the modulation of the sweep field, for example in the form of a whole number fraction or a multiple.

Referring now to the drawings, FIG. 1 shows a diagrammatic perspective representation of a device for nuclear magnetic resonance therapy 1.

The device for nuclear magnetic therapy 1 comprises a table 2 on which the user can lie and rest his head on the head support 4.

The device includes the two side parts 5 and 6 which in this embodiment are curved in shape and which are arranged at the edge of the table 2.

Table 2 and side parts 5 and 6 are arranged on a support 7 on which a control device 8 is also arranged.

A coil is located in each of the side parts 5 and 6. The sweep field is created by these coils. The coils (not represented) are activated by the control device.

A further coil (not represented) is arranged under the table 2 and creates an alternating magnetic field which overlays the sweep field at a right angle.

The device for nuclear magnetic resonance therapy also includes a device for stretching the user 3. This comprises a strap 9 which is positioned around the user's hips and a strap 10 which is positioned under the shoulders and around the upper part of the user's body.

The strap 9 is connected via a connecting strap which runs over pulleys 13 at the end of the table with a pulling device 12 which is powered by a motor.

It is to be understood that the connecting straps 11 can have any design and that ropes or chains are possible.

The pulling device 12 is also activated by the control device 8. The straps 9 and 10 can be pulled in opposing directions and thus exercise a force on the user's spinal column 3.

In this embodiment, the strap 10 is also connected to a further pulling device (not represented) via a connecting strap 11 which runs over pulleys. However, it is to be understood that one pulling device is sufficient to apply a force.

The use of the pulleys has the advantage that the pulling device 12 does not have to be mounted on or directly adjacent to the table.

In particular it is also possible in the case of a pulling device with a compact form that the pulleys 13 are not needed and the pulling device can be located at the end of the table.

The control device 8 includes an operator interface or a slot for a chip card by which a treatment can be started and executed automatically. At this time the control device 8 controls both the sweep coils located in the side parts 5 and 6 and the coils for creating the alternating magnetic field as well as the pulling device 12.

Thus, a periodically changing force can be created in particular by the pulling device 12. This force can in particular be synchronized with the modulation frequency of the sweep field.

Figure 2:
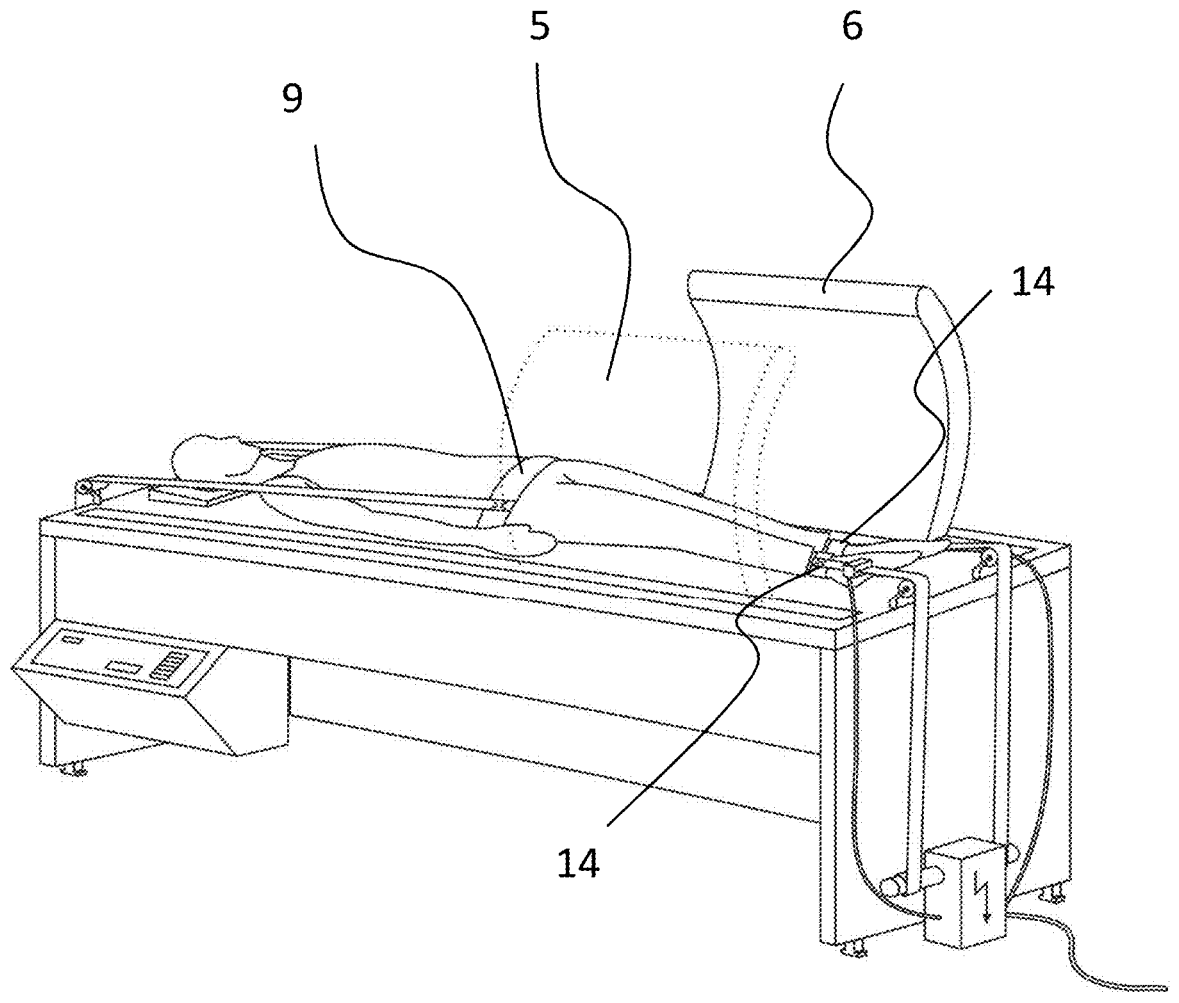
FIG. 2 illustrates a further perspective view of an exemplary embodiment of the device which also comprises actuators for concentrating a vibration on the pulling device.

FIG. 2 shows a variant of the embodiment which corresponds to FIG. 1 except for the differences described further herein.

Unlike FIG. 1, the user's legs are stretched in the representation in FIG. 2. In order to achieve this, the device for stretching comprises the strap 9 which is fastened around the user's hips and the straps 14 which are fastened around the user's ankles.

The side parts 5 and 6 are now arranged in the region of the user's legs.

It is also possible in particular that the side parts 5 and 6 are arranged so they can be moved in relation to the table. In this way the device can be altered to treat legs or the spinal column.

It is to be understood that an alternating coil must be located under the legs. In order to achieve this, it is conceivable that either the alternating coil must be designed to be movable or that several alternating coils are to be provided under the table.

Figure 3:
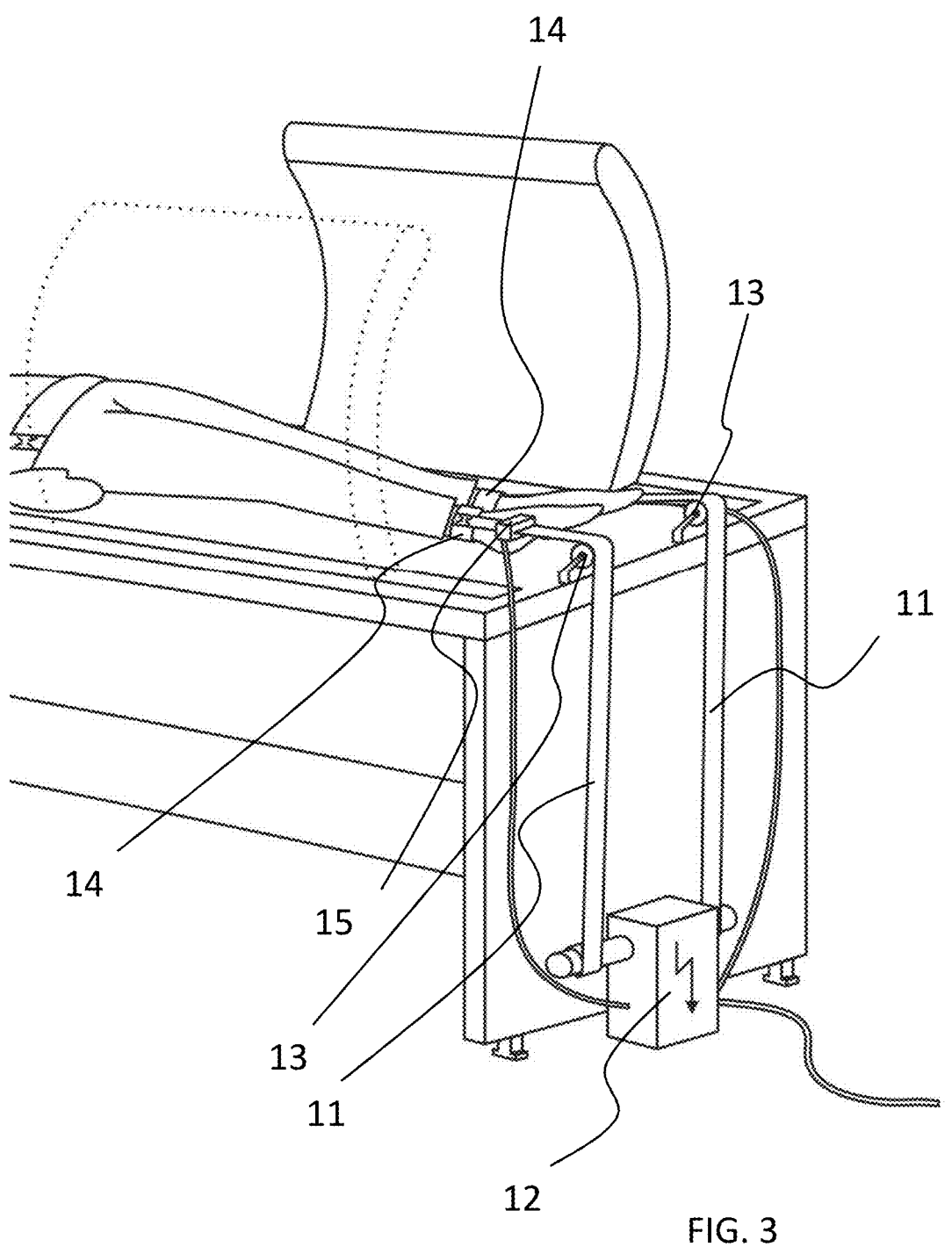
FIG. 3 is a detailed representation of FIG. 2.

FIG. 3 shows a detailed representation of FIG. 2 in which it can now be seen that the connecting strap 11 includes actuators 15 which are arranged directly next to the straps 14 which are fastened around the ankles.

It is also conceivable that the actuators 15 can be integrated into the straps.

Seen from the pulling device 12, the actuators are consequently arranged after the pulleys and thus close to the user.

The actuators 15 operate, for example, on the electromagnetic principle and are, for example, arranged as moving coil actuators. A periodically varying force can be created by the actuators by periodically moving a weight to and fro; this force is overlaid with the force of the motorized pulling device 12.

To achieve this, in this embodiment the actuators 15 are connected with the control device (8 in FIG. 11) via the pulling device 12. In particular, vibrations of a higher frequency can be created via the actuators to modulate the force. On the one hand this would be more difficult via the pulling device 12 which is powered by a motor and in particular in the case of higher frequency vibrations there would be the danger that as a result of damping effects in the connecting straps 11 the modulation of the force would no longer reach the straps 14.

Figure 4:
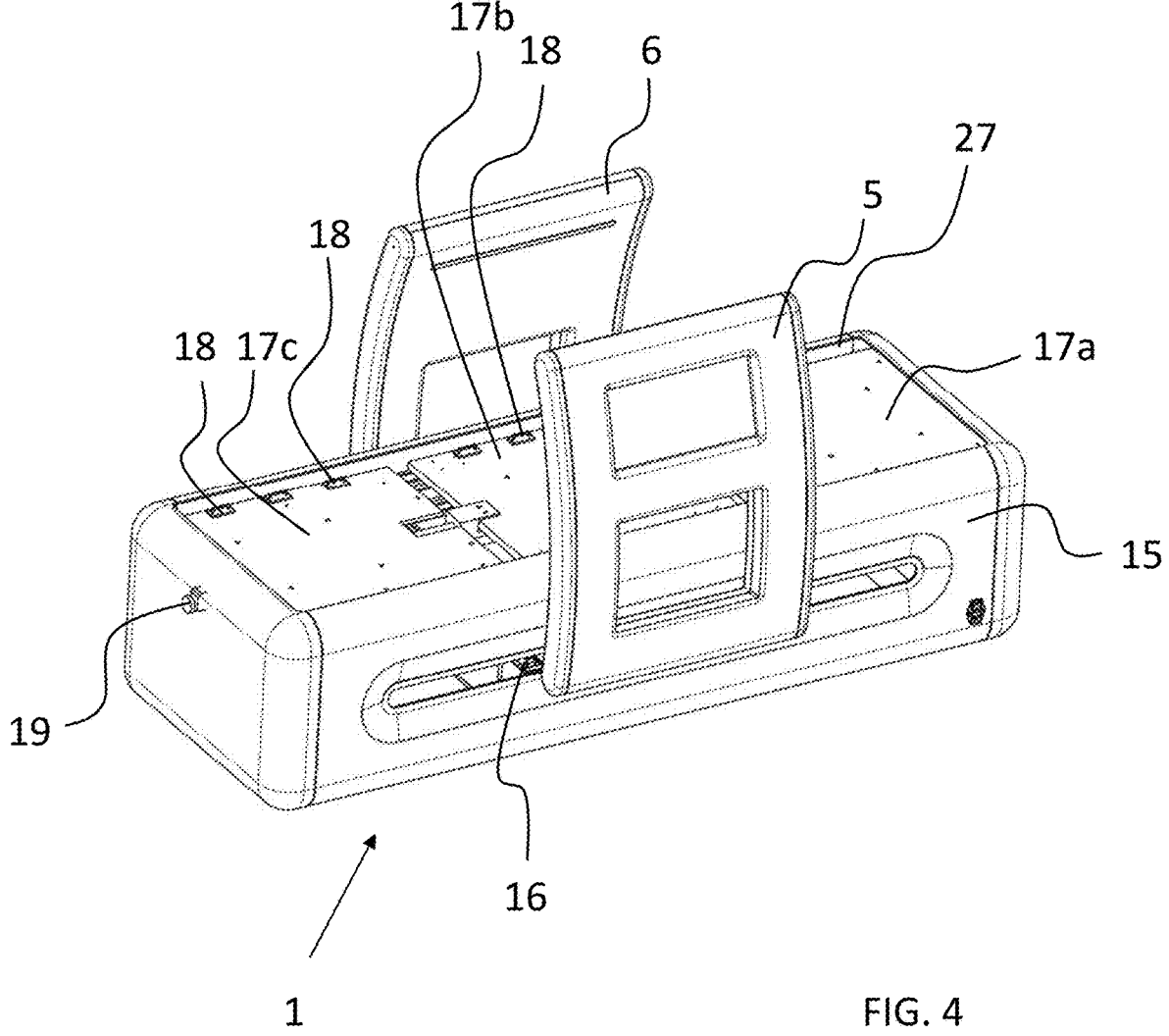
FIG. 4 is a perspective view of an exemplary embodiment of the device fitted with a module for nuclear magnetic resonance therapy.

In a perspective drawing, FIG. 4 shows a device 1 for nuclear magnetic resonance therapy 1. In this embodiment the table of the device for nuclear magnetic resonance therapy is formed by the boards 17a to 17c.

The central board 17b is designed to move in relation to the other boards 17a, 17c.

It is to be noted that the boards 17a to 17c can include a padding which is not shown here.

Figure 5:
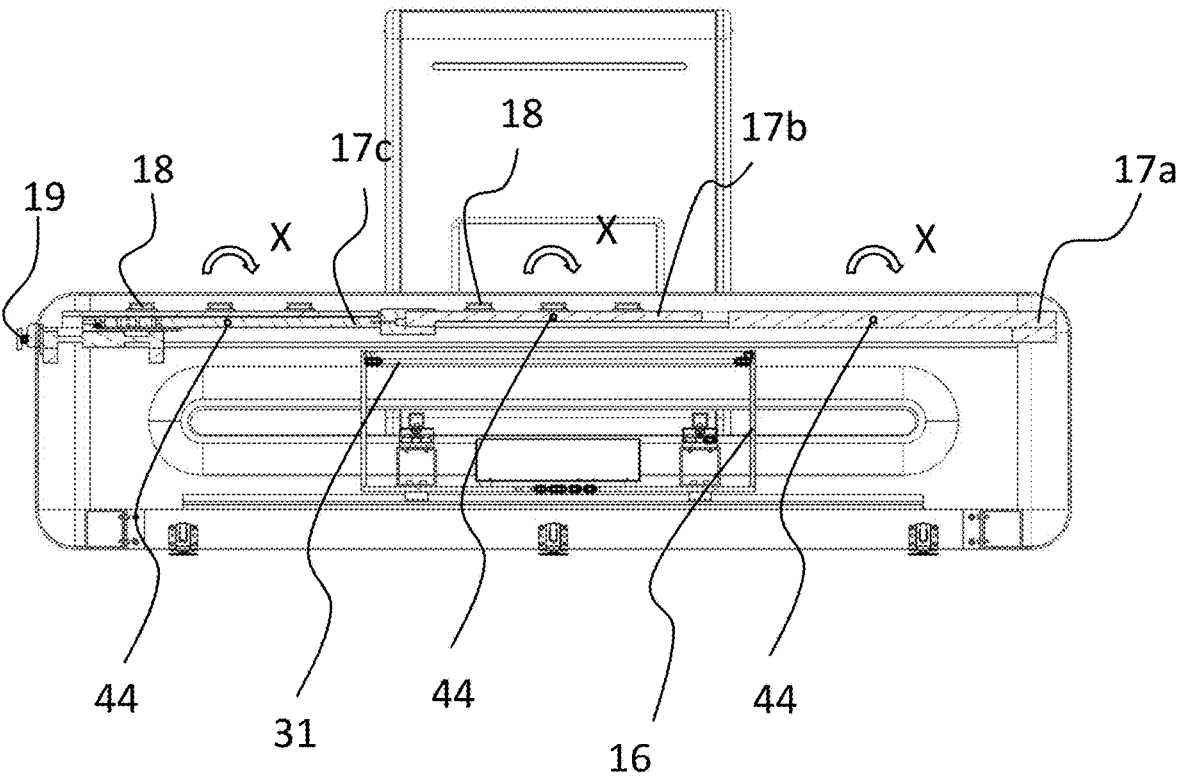
FIG. 5 is a sectional view along the main direction of stretching.

In an embodiment shown in FIG. 5 which comprises not only the boards 17a to 17c which are explicitly shown but can also comprise up to five or more boards as possible individual boards, thus two or more additional boards but which are not shown in FIG. 5 for the sake of simplicity, a transverse bearing point 44 or bearing post 44 is provided in particular at a right angle to the longitudinal direction of the boards 17a to 17c in order to enable a displacement, in particular a tilting of the individual boards of the table around the axis of the bearing point 44 and hence in a positive or negative direction of the arrow X shown in FIG.

5 by mechanical or electrical means. In this way it is possible to specifically reach a portion of the spinal column and in particular to reach individually affected vertebrae in the best possible quality and intensity of the stretching for the affected vertebrae.

In order to make tilting of this nature possible, the assemblies located under the module 30 or the table 1 can be positioned somewhat lower than shown in the drawings and in this way do not have to be in the way of the tilting.

Because of the sweep field this is not important for the overall resultant field configuration and the success of the treatment being sought.

In this embodiment of the invention the device for nuclear magnetic therapy 1 comprises the side parts 5 and 6 which are arranged on a movable carriage.

Coils capable of creating a magnetic field extending transversely to the table are again to be found in the side parts 5, 6.

A further coil (not represented) is located in the carriage 16 under the table. An alternating field is directed by this coil into the treatment zone which runs transversely to the field and which is created by the coils located in the side parts 5, 6.

In order to stretch the user, the boards 17b and 17c have eyelets through which straps can be passed.

In an embodiment of the invention it is also envisaged that one of the boards is provided with an elevation, particularly an elevation in the form of a wedge (not represented) on which the user can elevate his feet.

In order to stretch the user, the middle board 17b can be moved horizontally by activating a drive 19 arranged on the end.

The drive may be designed in such a way that the distance of movement is restricted to less than 50, preferably less than 5 cm to ensure that the device 1 is safe even in the event of errors by the user.

In this embodiment the mechanism for stretching the user is designed as a module which can be retrofitted and which comprises a frame 27 with the boards 17a to 17c which can be placed on the casing 15 of the device 1 for nuclear magnetic resonance therapy.

FIG. 5 is a sectional view along the main direction of stretching of the device for nuclear magnetic resonance therapy 1 shown in FIG. 4.

In particular the three boards 17a to 17c arranged behind each other can be seen; of these three, the middle board 17b can be moved horizontally.

The movable carriage with the side parts and a coil 31 for creating an alternating magnetic field can also be moved.

The board 17b can be moved to and fro by the drive 19 arranged on the end.

Figure 6:
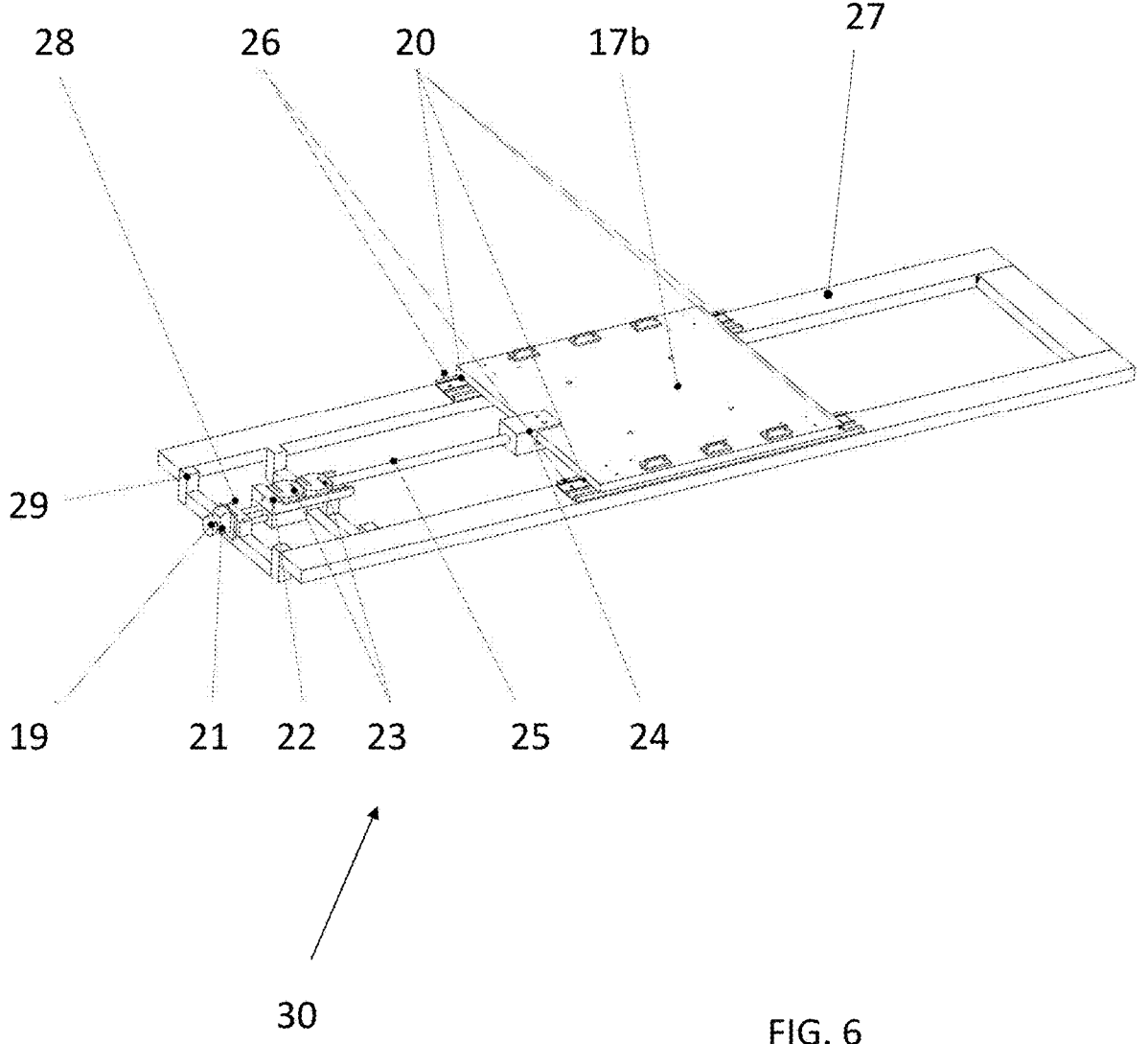
FIG. 6 shows, in a perspective view, the module that can be retrofitted.

FIG. 6 is a perspective view of the module 30 which comprises a frame 27 which can be placed on a casing.

The front and rear board (17a and 17c in FIG. 5) have been omitted from this view.

The center board 17b comprises guides 20 by which the center board 17b can be moved along the frame 27 on rails 26.

The rails 26 are mounted on the frame.

The drive 19 is mounted on a strut 29 of the frame in order to move the center board 17b.

The drive 19 comprises a spindle 28 by which a carriage 22 can be moved.

The carriage 22 which is located under the front board (17c in FIG. 5) is linked to the center board 17 by a connector 24 via a bar 25.

Thus the carriage 22 is moved by the drive 19 and then itself moves the movable board via the bar 25.

The module 30 also comprises a force measurement device.

In this embodiment the force sensors 23, in particular formed as S-shaped load cells, are mounted on the carriage 22.

The force measurement device may therefore also be placed under a board (17c).

The force measured by the force sensor 23 is shown on a display 21.

The display 21 can take the form of a force display and/or a position display.

In particular, the upward movement by which the center board 17b is moved can be determined by the display 21.

It is also possible to provide the display 21 with an operating device via which, for example, a program can be started which periodically moves the board 17b by a drive powered by an electric motor.

A control device for the drive can in particular also act in conjunction with the force sensor 23, for example in such a way that the upward movement is controlled as a function of the force.

Figures 7, 8:
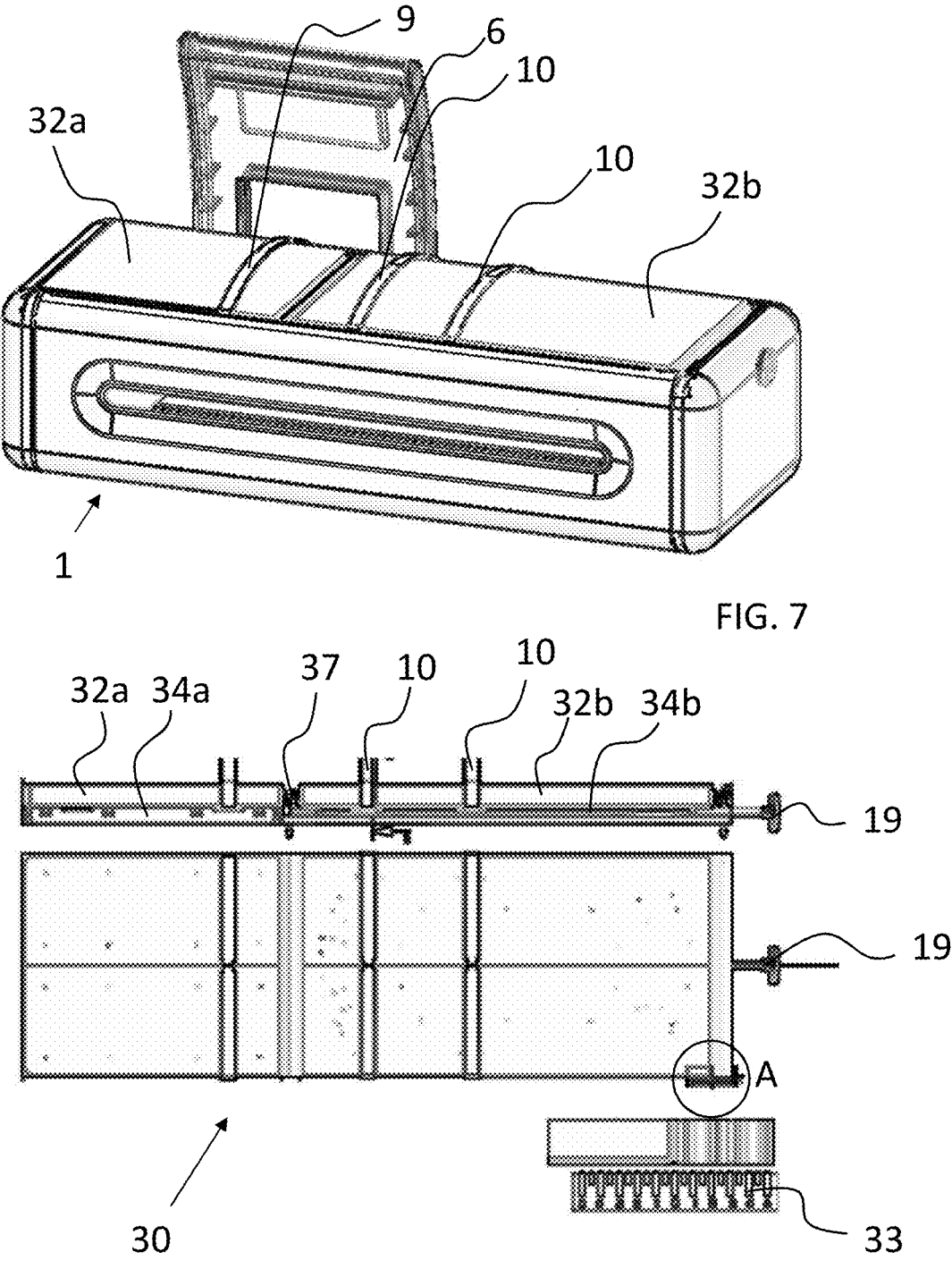
FIG. 7 is a perspective view of an exemplary embodiment of a device for nuclear magnetic resonance therapy.
FIG. 8 is a plan view and a side view including a detailed representation of a scale of the device of FIG. 7.

FIG. 7 shows in a perspective drawing a device 1 for nuclear magnetic resonance therapy which comprises side parts 6 corresponding to the embodiments described earlier.

The opposite side part has been omitted in this view to improve clarity.

The device 1 for nuclear magnetic resonance therapy is also modular in design and comprises a table composed of the pads 32a and 32b.

The table is therefore divided into two areas which can be moved in relation to each other to stretch the user.

A strap 9 is positioned under the pad 32a.

Two straps 10 which are spaced apart from each other lie over the pad 32b.

The pads 32a and 32b are part of an attachable module which is represented in a plan view and a side view in FIG. 8.

The module 30 includes the rails 34a and 34b on which the pads 32a and 32b are arranged.

It is possible to move the rail 34b and thus pad 32b, along with the straps, in relation to the pad 32a by means of a drive 19, shown in this embodiment as a manual drive.

In this embodiment the drive 19 can be positioned on the narrow end of the module 30.

As can be seen in the detailed representation of area A below on the right, a scale 33 is positioned at the edge from which the movement of the carriage, which is positioned on the rails 34b, can be read.

Thus the stretching of the user can be read off via the scale 33.

Figure 9:
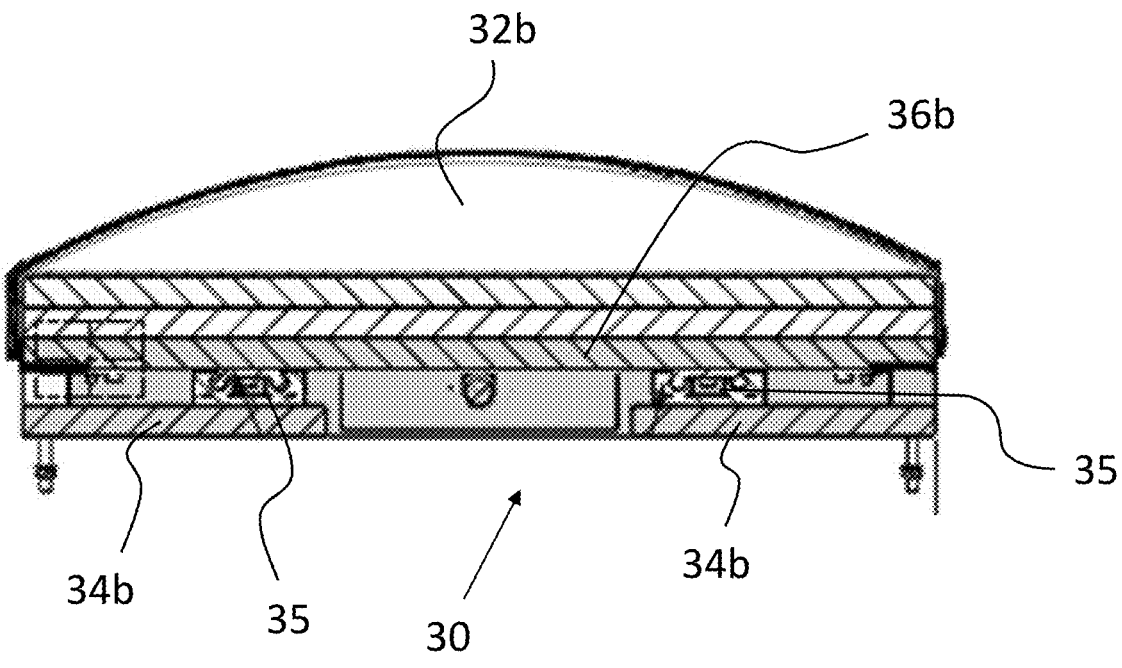
FIG. 9 is an axial sectional view of the device of FIGS. 7-8.

FIG. 9 is an axial sectional view of the module 30.

The board 36b is positioned on the rails 34b over the bearing 35 such that it can be moved in a linear direction.

The board 36b can thus be moved with the pad 32b.

Figure 10:
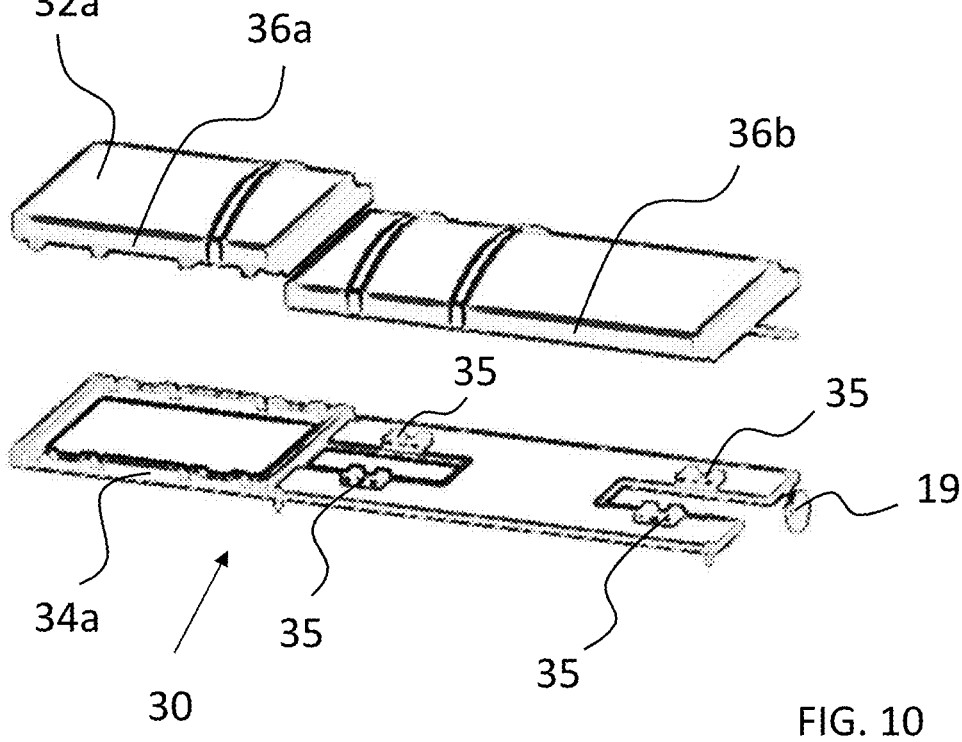
FIG. 10 shows an exploded representation of the components of the module which is used for stretching the user and represented in FIGS. 7 to 10.

FIG. 10 is an exploded representation of the components of the module.

The rails 34a are part of a frame on which a head part with the pad 32a and the board 36a can be placed.

In this embodiment this head part is connected rigidly with the remainder of the device for nuclear magnetic resonance therapy and is therefore not moved for stretching the user.

On the other hand the board 36b is movable along the main stretching direction on the bearings 35 in an axial direction; in this embodiment this movement is achieved by means of the spindle drive 19.

The two parts with the pads 32a and 32b which can be moved compared with each other are connected to each other by the link 37 as shown in FIG. 8. The link 37 can, for instance, take the form of a concertina-like foldable plastic part which permits movement in several planes and directions in relation to the other movable parts. The link 37 closes the gap between the parts which occurs during the stretching in such a way that dirt and foreign bodies cannot penetrate to the device underneath.

Although not shown explicitly in the drawings, a link of this nature can be arranged between all the boards, for example in the longitudinal direction of the module 30 or the table 2.

Figure 11:
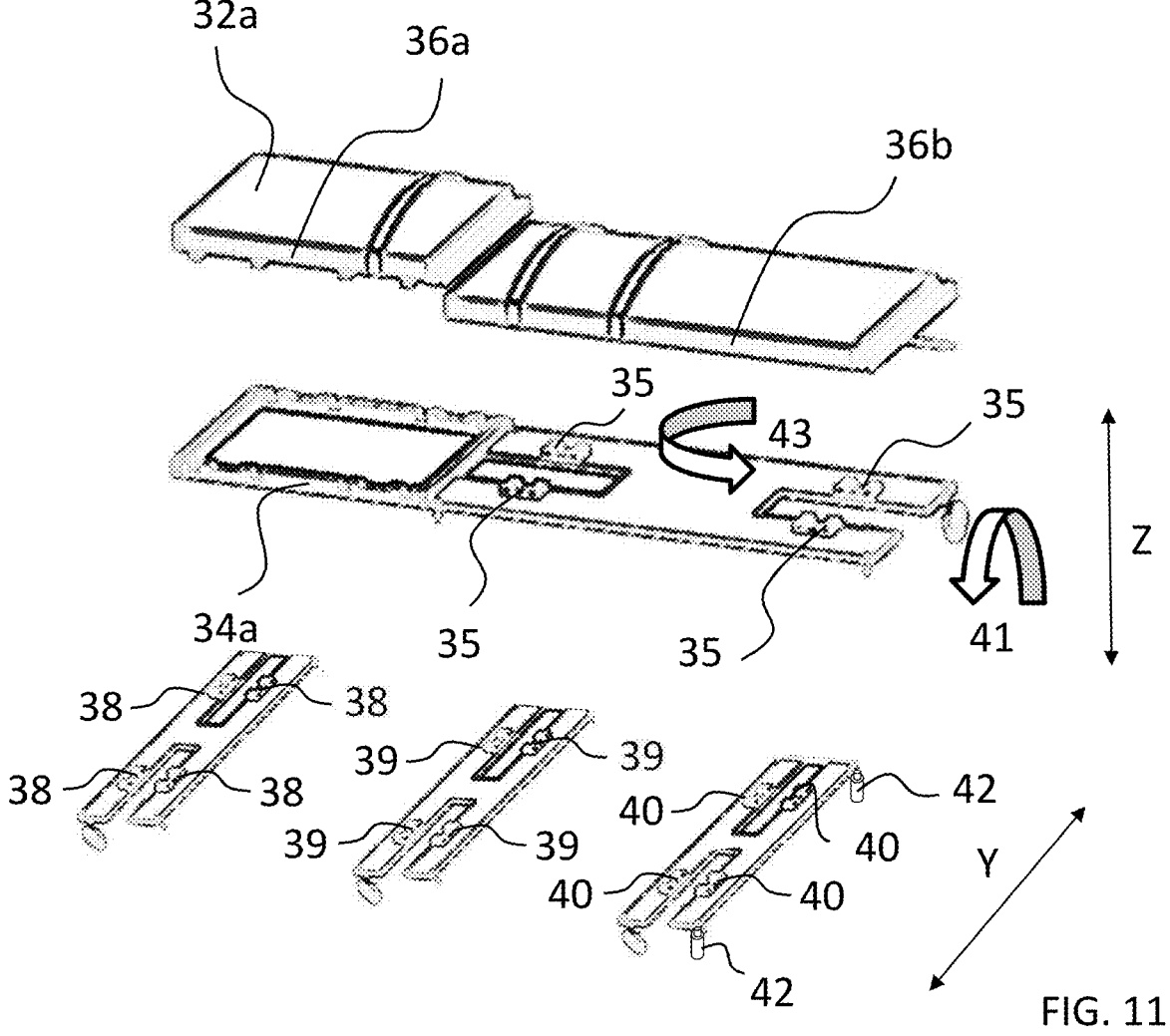
FIG. 11 is a further exploded view that shows the components of the module used for the device illustrated in FIGS. 7 to 10 for stretching the user in which the stretching can be set in three planes or directions.

Reference is made further herein to FIG. 11. In a further exploded representation, this shows the components of the module which are used for the device represented in FIGS. 7 to 10 for stretching the user and in which, however, the stretching can be set in three planes or directions.

By way of further bearings 38 the head part with the pad 32a and the board 36a can be moved vertically in relation to their longitudinal direction, and thus in the linear direction of the arrow Y. By way of the bearings 39 and 40 the board 36b can also be moved vertically in relation to its main stretching direction and thus in the linear direction of the arrow Y.

By way of the bearings 39 and 40 it is also possible to rotate the board 36b round in the direction of rotation indicated by arrow 40 at least in small angular ranges, particularly through a non-identical movement using the bearing 39 relative to the bearing 40. In the framework of the present disclosure it is possible to arrange the board 36b on a rotatable bearing in addition to or as an alternative to the bearings 38 and 39 in order to permit larger angles in the direction of rotation indicated by arrow 43.

The board 36b can be lifted or lowered in the direction of the arrow z with additional linear translators 42 at its distal end. If the linear translators 42 are activated differently, it is also possible to rotate the board in the direction indicated by the arrow 41.

Thus the board 36b can be moved independently in at least three directions of the space: the first direction is to be understood as the direction along its longitudinal axis, and the second direction the direction represented as direction y in FIG. 11, running horizontally and transversely to its longitudinal axis, in particular running horizontally to its longitudinal axis under a vertical angle of 90°, and the third direction as the direction indicated by the arrow Z in FIG. 11 running vertically and transversely to its longitudinal axis, in particular under a vertical angle of 90°, whereby in this direction it may be provided that only the distal end of board 36b is raised on which the linear translators 42 are arranged and hereby the board 36b can be raised and lowered at its distal end and thus its foot end.

In addition, the board can be moved independently also in at least two directions which are orthogonal to each other. These are the directions indicated by the arrows 41 and 43.

In avionics the direction of rotation indicated by the arrow 41 is, for instance, also called a "roll" or "roll direction" and the direction indicated by the arrow 43 is also called "yawing" or "yaw direction".

In sum, the board can therefore be moved independently in three orthogonal spatial directions, in particular defined and set in their position.

It is in the framework of the present disclosure that although some embodiments offer all the above possibilities of movement, nevertheless all subordinate combinations of the present disclosure which only present one or a part of the possibilities of movement mentioned above are included.

In particular, success in the treatment of patients with arthrosis can be significantly improved by embodiments provided according to the invention.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

REFERENCE NUMBER LIST

1 Device for nuclear magnetic resonance therapy
2 Table
3 User
4 Head support
5 Side part
6 Side part
7 Support
8 Control device
9 Strap
10 Strap
11 Connecting strap
12 Pulling device
13 Pulley
14 Strap
15 Casing
16 Carriage
17a-17c Board
18 Eyelet for a strap
19 Drive
20 Guide
21 Display
22 Carriage
23 Force sensor
24 Connector
25 Bar
26 Rail
27 Frame
28 Spindle
29 Strut
30 Module that can be retrofitted
31 Coil
32a Pad
32b Pad
33 Scale
34a Rail
34b Rail
35 Bearing
36a Board
36b Board
37 Connection
38 Bearing
39 Bearing
40 Bearing
41 Arrow indicating a direction of rotation
42 Linear translator
43 Arrow indicating a direction of rotation
44 Bearing point or bearing bar X Arrow indicating a direction, particularly a direction of tilt Y Arrow indicating a direction, particularly a direction of movement Z Arrow indicating a direction, particularly a direction of movement

What is claimed is:

1. A device for nuclear magnetic resonance therapy, comprising:
   a device configured to create an alternating magnetic field;
   a device configured to create a magnetic field as a sweep field running transversely to the alternating magnetic field; and
   a device configured to stretch a user.

2. The device for nuclear magnetic resonance therapy of claim 1, wherein the device configured to stretch the user comprises straps for use as well as at least one pulling device for a belt.

3. The device for nuclear magnetic resonance therapy of claim 1, wherein the device configured to stretch the user comprises a movable board.

4. The device for nuclear magnetic resonance therapy of claim 3, wherein the movable board is movable by a drive on a narrow end of the movable board.

5. The device for nuclear magnetic resonance therapy of claim 1, wherein a periodically changing force can be created by the device configured to stretch the user.

6. The device for nuclear magnetic resonance therapy of claim 5, wherein a frequency of the periodically changing force is 5 to 1 kHz.

7. The device for nuclear magnetic resonance therapy of claim 1, wherein the device configured to stretch the user comprises an actuator for creating a vibration on a pulling device.

8. The device for nuclear magnetic resonance therapy of claim 7, wherein the actuator is configured to vibrate with a frequency of between 1 and 500 Hz.

9. The device for nuclear magnetic resonance therapy of claim 1, further comprising a control device for the device configured to create an alternating magnetic field and configured to control the sweep field as well as control the device configured to stretch the user.

10. The device for nuclear magnetic resonance therapy of claim 9, wherein a frequency created by a pulling device is connected to a frequency of the sweep field by the control device.

11. The device for nuclear magnetic resonance therapy of claim 1, wherein at least one of the following is satisfied:
   the device for nuclear magnetic resonance therapy further comprises a table for the user comprising two side parts each with a coil arranged at a side of the table and form part of the device configured to create the sweep field; or
   the device configured to stretch the user includes a force measurement device.

12. A process for controlling a device for nuclear magnetic resonance therapy, the process comprising:
   creating an alternating magnetic field and a static sweep field transverse to the alternating field by which nuclear magnetic resonances are created in a tissue of a user; and
   stretching the user by a pulling device activated by a control device during the creation of the nuclear magnetic resonances.

* * * * *